(12) United States Patent
Terada et al.

(10) Patent No.: US 8,913,843 B2
(45) Date of Patent: Dec. 16, 2014

(54) IMAGE PROCESSING METHOD AND COMPUTER PROGRAM

(75) Inventors: Toshihiko Terada, Kyoto (JP); Hironori Yamauchi, Shiga (JP)

(73) Assignees: Takumi Vision Co., Ltd., Shiga (JP); Rohm Co., Ltd., Kyoto (JP)

( * ) Notice: Subject to any disclaimer, the term of this patent is extended or adjusted under 35 U.S.C. 154(b) by 586 days.

(21) Appl. No.: 13/142,892

(22) PCT Filed: Dec. 24, 2009

(86) PCT No.: PCT/JP2009/071499
§ 371 (c)(1),
(2), (4) Date: Jun. 30, 2011

(87) PCT Pub. No.: WO2010/079700
PCT Pub. Date: Jul. 15, 2010

(65) Prior Publication Data
US 2011/0280464 A1    Nov. 17, 2011

(30) Foreign Application Priority Data
Jan. 6, 2009  (JP) .................................. 2009-001187

(51) Int. Cl.
| G06K 9/00 | (2006.01) |
| G06K 9/40 | (2006.01) |
| A61B 6/00 | (2006.01) |
| G06T 5/00 | (2006.01) |
| G06T 7/00 | (2006.01) |

(52) U.S. Cl.
CPC ..... *A61B 6/5217* (2013.01); *G06T 2207/20012* (2013.01); *G06T 5/008* (2013.01); *G06T 7/0081* (2013.01); *A61B 6/502* (2013.01)
USPC ............................ 382/274; 382/128; 382/260

(58) Field of Classification Search
None
See application file for complete search history.

(56) References Cited

U.S. PATENT DOCUMENTS

| 5,732,121 | A | 3/1998 | Takeo et al. | |
| 6,031,928 | A * | 2/2000 | Scott | 382/108 |
| 6,771,793 | B1 * | 8/2004 | Yamada | 382/264 |
| 7,386,183 | B2 * | 6/2008 | Tamura | 382/260 |

(Continued)

FOREIGN PATENT DOCUMENTS

| JP | 09-167238 | 6/1997 |
| JP | 10-289318 | 10/1998 |
| JP | 2005-052295 | 3/2005 |
| JP | 2005-198890 | 7/2005 |

(Continued)

*Primary Examiner* — Matthew Bella
*Assistant Examiner* — Jose M Torres
(74) *Attorney, Agent, or Firm* — Fish & Richardson P.C.

(57) ABSTRACT

To assign angle-dependent information to an input image in order to highlight and display one-dimensional patterns. First, data of an input image is inputted to a computer (Sa1). An arbitrarily defined constant m is then inputted as a contrast intensity (Sa2). Next, a closed region (x, y) made up of a plurality of pixels in the input image is demarcated as a target region D, degrees of inclination between respective two pixels, namely, a pixel of interest in the target region D and arbitrarily defined neighboring pixels thereof, are summed over a whole circumference around the pixel of interest, and the sum is divided by the number of pixels within the target region to calculate a mean value thereof (Sa3). Furthermore, an amplitude value β of a gradient obtained in step (Sa3) is multiplied by the contrast intensity m (where m is a positive constant) inputted in step (Sa2) and an arbitrarily defined offset value γ is added to the obtained value (Sa4) to obtain a final output image (Sa5).

2 Claims, 12 Drawing Sheets

(56) References Cited

U.S. PATENT DOCUMENTS

| | | | |
|---|---|---|---|
| 2001/0008418 A1* | 7/2001 | Yamanaka et al. | 348/222 |
| 2006/0098854 A1 | 5/2006 | Oosawa | |
| 2007/0242153 A1* | 10/2007 | Tang et al. | 348/365 |
| 2009/0003722 A1* | 1/2009 | Nadabar et al. | 382/255 |
| 2009/0118614 A1 | 5/2009 | Sendai | |

FOREIGN PATENT DOCUMENTS

| | | |
|---|---|---|
| JP | 2006-130049 | 5/2006 |
| JP | 2006-130212 | 5/2006 |
| JP | 2006-325937 | 12/2006 |
| JP | 2008-161283 | 7/2008 |

* cited by examiner (a)

| 1 | 1 | 1 |
|---|---|---|
| 1 | -8 | 1 |
| 1 | 1 | 1 |

(a)

(b)

(c)

(a)

(b)

IMAGE PROCESSING METHOD AND COMPUTER PROGRAM

BACKGROUND OF THE INVENTION

1. Field of the Invention

The present invention relates to a digital image processing method and a computer program for extracting a particular portion included in a digital image to be highlighted and displayed or, conversely, to be removed.

2. Description of the Related Art

In a digital image, when comparing a pixel of interest and a neighboring pixel, a vector expressing information related to a change in digitalized image signals (for example, luminance values) of both pixels is generally referred to as a "differential image" or a "gradient image" (in the present specification, the term "differential image" will be uniformly used). A differential image represents a "gradient vector" calculated when comparing two points (two pixels), namely, a pixel of interest and an arbitrarily defined neighboring pixel thereof from respective changes in coordinates and digital values. An "iris filter" is known as an image processing algorithm utilizing a gradient vector. With an iris filter, after obtaining a gradient vector thereof, a "degree of concentration" of an image signal (for example, a luminance value) digitalized from the gradient vector is calculated. Systems for supporting interpretation of a mammographic image by applying threshold processing to the degree of concentration and other calculated values have been disclosed (for example, refer to Japanese Patent Laid-Open No. H09-167238, Japanese Patent Laid-Open No. H10-289318, Japanese Patent Laid-Open No. 2005-52295, and Japanese Patent Laid-Open No. 2006-130049).

An interpretation system of this type is designed based on a model in which a luminance value of a mass shadow decreases radially (in other words, a mass shadow is characteristically brighter toward a center thereof and darker toward a periphery thereof).

However, in reality, mass shadows have various shapes and are not necessarily so simple as to be comprehensively solved by a model such as that described above. The interpretation system described above functions properly for extremely typical mass shapes such as a "normal distribution" whose luminescent spot peaks at a center of the mass. However, at present, the interpretation system is nowhere near a practical level from a comprehensive perspective and is considered to be merely a supplementary tool for diagnostics.

In other words, with mammography interpretation, there are many cases where even a physician with sufficient experience may hesitate to make a decision. While the Japan Radiological Society has formulated a guideline in an attempt to standardize an interpretation method or the like of mammography diagnostics for the purpose of detecting breast cancer, this itself is indicative of how difficult it is to determine a mass.

In particular, with respect to the discovery of a mass in mammography diagnostics of mammary glands, it is extremely difficult to distinguish a simple overlapping of mammary glands from a true mass. In reality, a shape, a boundary and a margin, a relative luminance on an image, and the like are comprehensively determined according to a decision tree of mass categories, and a final diagnosis is made by additionally considering results of other diagnostic approaches.

The present invention has been made in consideration of the above, and a main technical object of the present invention is to provide a novel image processing method and image processing program enabling a characteristic portion in a digital image to be highlighted and displayed.

SUMMARY OF THE INVENTION

An image processing method according to the present invention provides three main novel processing methods.

A first invention and a second invention according to the present invention are image processing methods for adjusting a size of an image signal of each pixel included in an input image by a computer according to a predetermined purpose, and a third invention according to the present invention is an image processing method for extracting a characteristic portion of an image signal of each pixel included in an input image by a computer and enclosing the characteristic portion with a closed curve.

The first invention includes the steps of: (Sa1) inputting data of an input image into a computer; (Sa2) inputting an arbitrarily defined constant m as a contrast intensity; (Sa3) demarcating a closed region (x, y) made up of a plurality of pixels in the input image as a target region D, summing degrees of inclination between respective two pixels, namely, a pixel of interest in the target region D and arbitrarily defined neighboring pixels thereof, over a whole circumference around the pixel of interest, and dividing the sum by the number of pixels within the target region to calculate a mean value thereof; and (Sa4) multiplying an amplitude value $\beta$ of a gradient obtained in step (Sa3) by the contrast intensity m (where m is a positive constant) inputted in step (Sa2) and adding an arbitrarily defined offset value $\gamma$ to the obtained value.

In the present invention, in step (Sa3), since a mean value of an amplitude value $\beta$ of a gradient is calculated by summing degrees of inclination between a pixel of interest and neighboring pixels thereof over a whole circumference around the pixel of interest and dividing the sum by the number of pixels within a target region, an angular component of the gradient is cancelled out and a difference image not including angular information and solely including an amplitude value is generated. Furthermore, since an amplitude value is further enhanced by multiplying by a contrast intensity m, the greater the difference in image signals between a pixel of interest and a neighboring pixel, the stronger the display.

An image signal is a scalar quantity expressing a luminance value or a gradation of a hue (for example, red/green/blue). Therefore, when the present invention is applied using a luminance value as an image signal, in particular, a one-dimensional pattern such as a linear pattern or a contour in an input image is to be highlighted and displayed in an output image.

With the first invention, by setting the target region D to five or more neighboring pixels of the pixel of interest, an amplitude value that takes into consideration image signals of neighboring pixels in a wider range can be calculated.

The second invention includes the steps of: (Sb1) inputting data of an input image into a computer; (Sb2) demarcating a closed region (x, y) made up of a plurality of pixels in the input image as a target region C, and calculating an angular component $\theta$ of a gradient vector obtained from coordinates of a pixel of interest in the target region C and an arbitrarily defined neighboring pixel thereof and the two pixels; and (Sb3) multiplying an absolute value of the angular component $\theta$ of the gradient vector by a predetermined constant to calculate a central image signal a in the target region C.

In the present invention, in step (Sb3), a central image signal $\alpha$ is expressed as a function of $\theta$ or, in other words, as a signal having angular dependency. Therefore, if a luminance value is set as an image signal, since luminance is expressed so as to have angular dependency in an output signal, a portion having a luminance gradient in the input image is three-dimensionally represented with a shadow and a characteristic portion of the input image is highlighted and displayed.

The third invention includes the steps of: (Sc1) inputting data of an input image into a computer; (Sc2) demarcating a closed region (x, y) made up of a plurality of pixels in the input image as a target region C, calculating coordinates of a pixel of interest in the target region C and an arbitrarily defined neighboring pixel thereof, calculating a size of a gradient vector from the two pixels, and calculating an angle θ between a unit vector oriented in a scanning direction of the target region C and the gradient vector; (Sc3) obtaining an inner product of the gradient vector and the unit vector, and normalizing the inner product to calculate a degree of concentration Z of the gradient vector; (Sc4) multiplying a filter based on second order differential such as a Laplacian filter and a Laplacian of Gaussian (LoG) filter; and (Sc5) applying a binarization process to step (Sc4) to obtain an output image.

With the third invention, after calculating a degree of concentration using an algorithm (Sc2 to Sc3) based on a known iris filter, edge detection is performed using a filter based on second order differential such as a Laplacian filter and a Laplacian of Gaussian (LoG) filter to enclose a contour of a portion with a high degree of concentration by a closed curve.

The third invention may be configured such that by repeating the steps for computing a degree of concentration using an iris filter (steps Sc2 to Sc3) twice or more, a characteristic point with a particularly high concentration of image signal values is extracted.

The first to third image processing methods according to the present invention can be realized as image processing application programs to be executed on a computer such as a personal computer.

The image processing method according to the present invention enables a characteristic of an input image to be extracted or highlighted and displayed. In addition, by removing an extraction result using known threshold processing, a pattern having a specific characteristic can be removed from the input image.

BRIEF DESCRIPTION OF THE DRAWINGS

FIG. 9 illustrates an example of a Laplacian filter (8-neighbor Laplacian filter);

DETAILED DESCRIPTION OF THE PREFERRED EMBODIMENTS

First Embodiment

Figure 1:
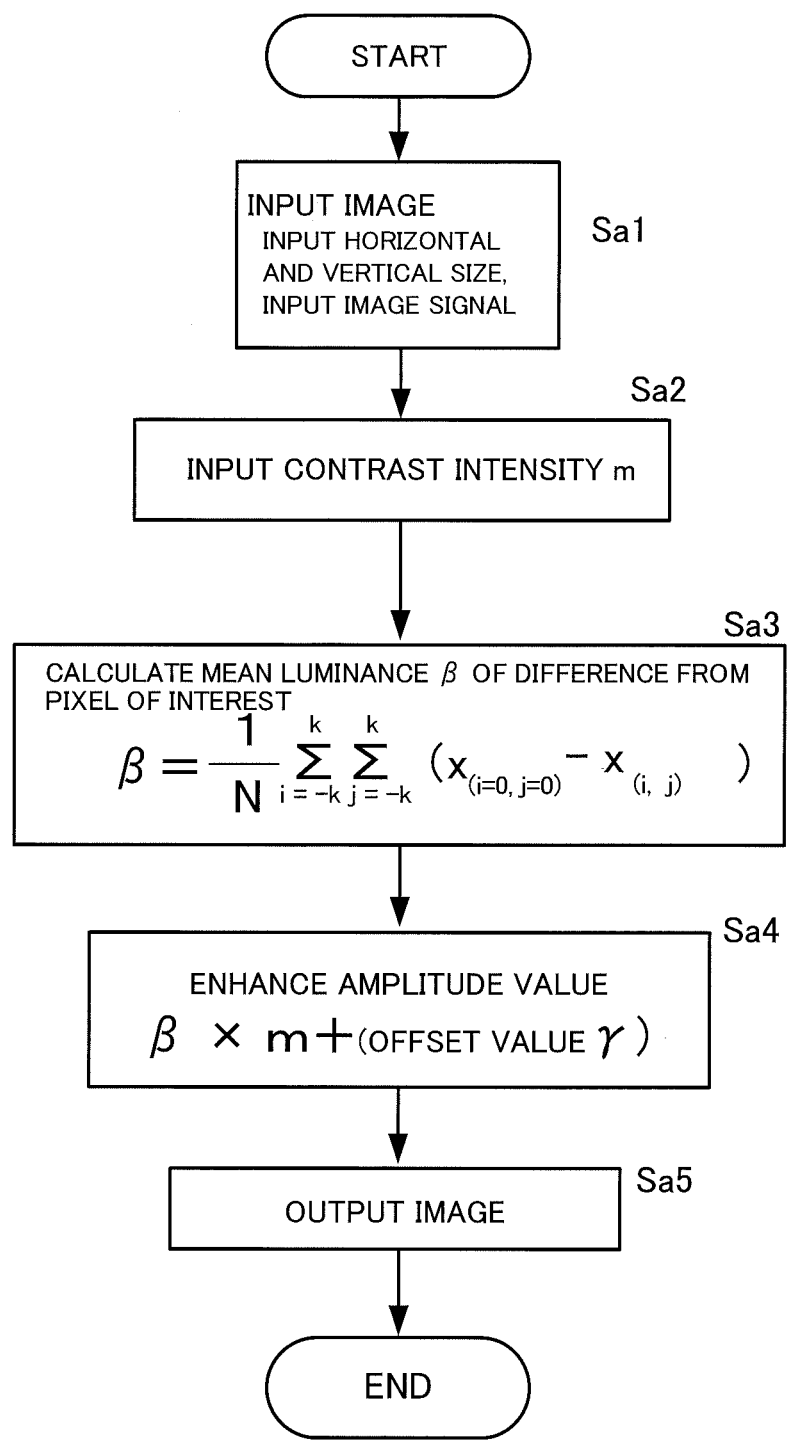
FIG. 1 is a diagram illustrating a procedure of an image processing method according to a first embodiment of the present invention.

Extraction Processing of a Characteristic Point Using an Amplitude Value of a Differential Image FIG. 1 is a diagram illustrating a procedure of an image processing method according to a first embodiment of the present invention.

Following a step (Sa1) for inputting data of an input image into a computer, a step (Sa2) for inputting an arbitrarily defined constant m as a contrast intensity is executed. The constant m is a positive constant for defining an intensity of contrast to be assigned to an output image.

Figure 2:
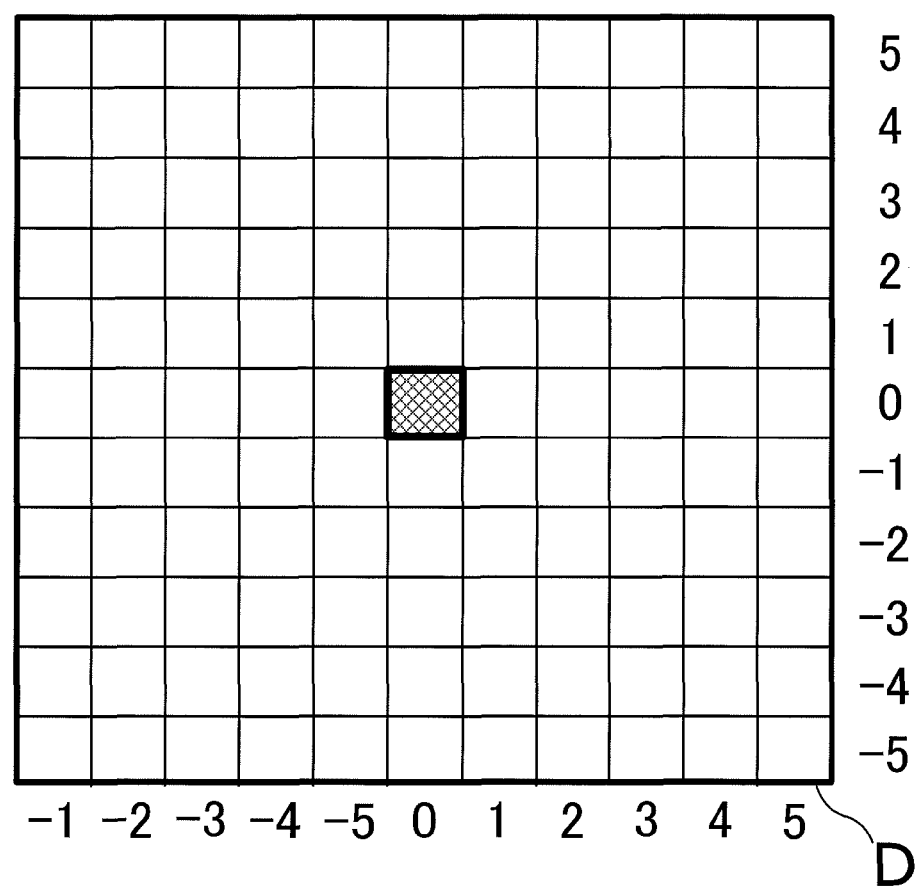
FIG. 2 illustrates a target region D in an image processing method according to a second embodiment.

FIG. 2 illustrates a target region D demarcating a closed region (x, y) made up of a plurality of pixels in the input image. In this example, five neighboring pixels of a center (pixel of interest) of the region are set as the target region. If a pixel of interest x (i=0, j=0), then an amplitude value β is defined as expressed in Expression 1.

$$\beta = \frac{1}{N} \sum_{i=-5}^{5} \sum_{j=-5}^{5} (X_{(i=0,j=0)} - X_{(i,j)}) \quad \text{[Expression 1]}$$

(N: number of pixels)

Generally, an amplitude value of a differential image is obtained separated into an x-component and a y-component. With such a method of calculating an amplitude value, an angular component of a gradient vector of a pixel of interest and a neighboring pixel must be calculated and a direction of a gradient must be set. However, simultaneously displaying an amplitude and an angle as images poses difficulties.

In consideration thereof, in the invention according to the first embodiment, a mean value of an amplitude value β of a gradient (in other words, a difference) of image signals of two pixels, namely, a pixel of interest in a target region D and each of arbitrarily defined neighboring pixels thereof, is calculated by summing degrees of inclination between the pixel of interest and neighboring pixels thereof over a whole circumference around the pixel of interest and dividing the sum by the number of pixels within the target region.

Due to such a method, since a directional component of a gradient is cancelled out, only an amplitude value of a pixel of interest is quantified, and a gradient not including angular information and only including an amplitude value is to be generated. In addition, since the wider the target region, the further the included pixels from a central pixel, an amplitude value that takes into consideration a wider range can be calculated.

When a luminance value is an image signal, an amplitude value β precisely expresses a luminance value of a pixel of interest. A positive β value indicates that the pixel of interest is to be displayed brighter than the surroundings, while a negative β value indicates that the pixel of interest is to be displayed darker than the surroundings.

In addition, by moving the target region D within the input image by predetermined pixel units, an amplitude value β of image signals of two pixels, namely, a pixel of interest in the target region and an arbitrarily defined neighboring pixel thereof, is sequentially calculated.

In a next step (Sa4), the amplitude value β obtained in step (Sa3) is multiplied by the contrast intensity m inputted in step Sa2 and an arbitrarily defined offset value is added. Step (Sa3) to step (Sa4) are repeated by moving the target region D within the input image in an x-direction and a y-direction (repetition) and, lastly, the amplitude value β calculated for each pixel is adapted to data of the input image to obtain an output image (step (Sa5)).

Figure 3:
FIG. 3(a) illustrates an example of an input image that is an original image of mammography according to the first embodiment.
FIG. 3(b) illustrates an example of an output image according to the first embodiment.
FIG. 3(c) illustrates another example of an output image according to the first embodiment.
Figure 3:
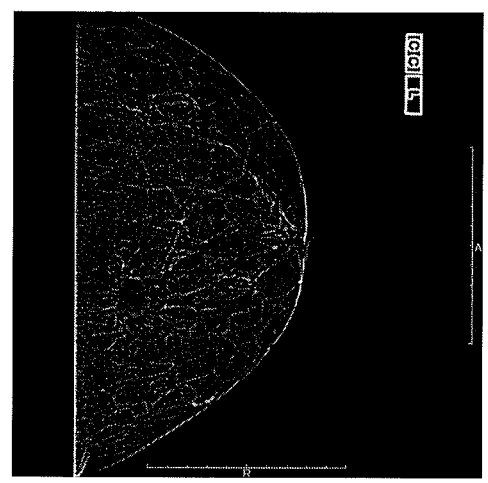
Figure 3:
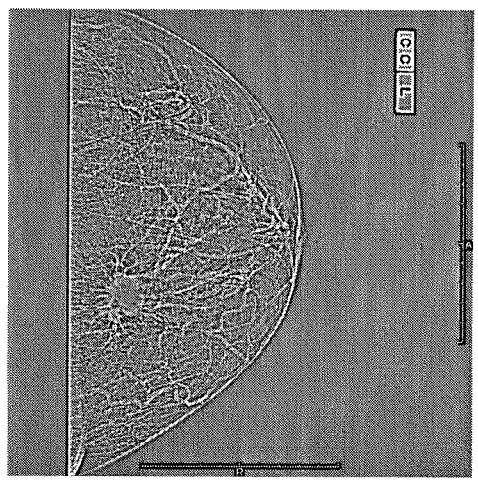

FIG. 3(a) illustrates an input image that is an original image of mammography. FIG. 3(b) illustrates an output image obtained by retaining only pixels having a positive amplitude value β as calculated according to Expression 1 in the image illustrated in FIG. 3(a), clipping luminance values to 0 for all other pixels, and subsequently multiplying the amplitude values β by 3.

FIG. 3(c) illustrates an output image obtained from the image illustrated in FIG. 3(a) by multiplying the amplitude value β calculated according to Expression 1 by 3 and adding 127 to all pixels as an offset.

In FIGS. 3(b) and 3(c), spiculae, mammary glands, and blood vessels that are inconspicuous in the original image are highlighted and displayed. In this manner, by calculating an amplitude value β and subjecting the amplitude value β to a linear transform using a linear function, one-dimensional patterns such as a linear pattern or a contour that are inconspicuous in the input image can be highlighted and displayed.

Second Embodiment

Stereoscopic Visualization Processing Using a Gradient Vector

Figure 4:
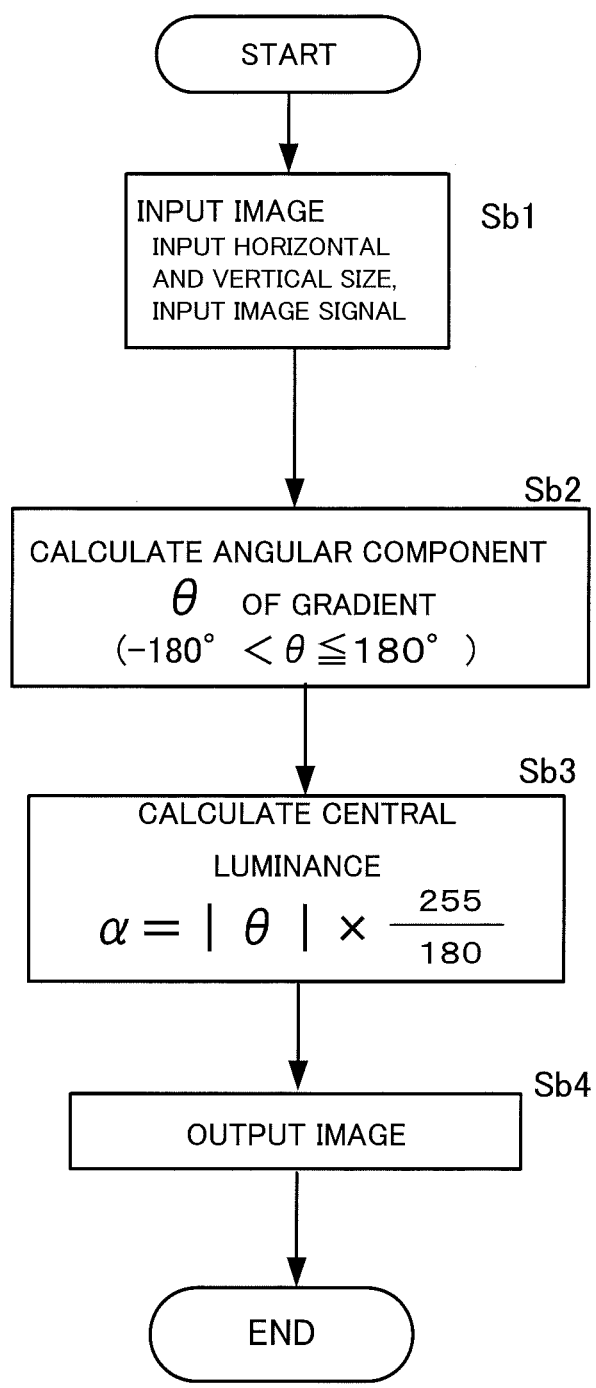
FIG. 4 is a diagram illustrating a procedure of an image processing method according to the second embodiment of the present invention.

FIG. 4 is a diagram illustrating a procedure of an image processing method according to a second embodiment of the present invention. Generally, a "gradient vector" is defined as a vector quantity for expressing a differential image having angular information. In the following description, it is assumed that an image signal represents luminance and a value of the image signal represents a luminance value. In addition, for convenience of description, a luminance value is to be expressed in 8 bits or, in other words, is to assume a value ranging from 0 to 255.

Figure 5:
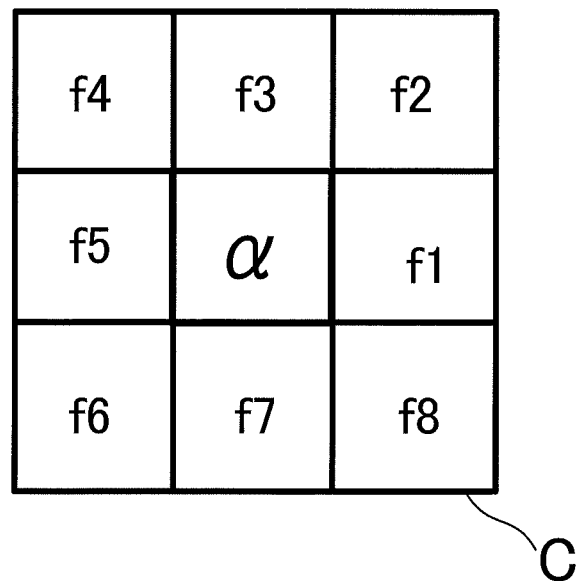
FIG. 5(a) illustrates an example of a target region C for obtaining a gradient vector.
FIG. 5(b) illustrates an example of a gradient vector in a case where an increment in an x-direction is 1 and an increment in a y-direction is −1 in FIG. 5(a)
Figure 5:
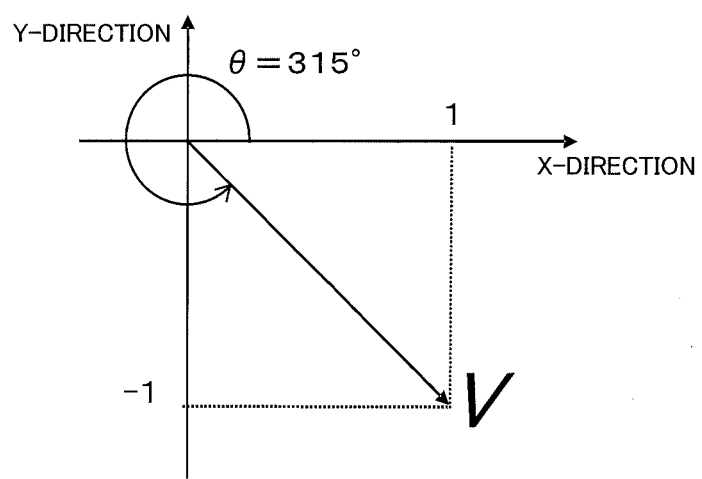

FIG. 5(a) illustrates a target region (mask) C provided in the input image. As an example, the target region C is set to a region of neighboring pixels that are one pixel away from a central pixel. In this case, a luminance value of a central pixel of the target region C is denoted by α and neighboring luminance values of the central pixel are respectively denoted by f1 to f8. Moreover, the target region may be set to a region of neighboring pixels that are any number of pixels away from the central pixel.

An angular component (inclination θ) of a gradient vector is generally expressed as an arc tangent of an increment in the y-direction (upward direction) with respect to an increment in the x-direction (rightward direction). For instance, with the example illustrated in FIG. 5(a), θ may be described as expressed in Expression 2.

$$\theta = \tan^{-1}\left\{\frac{(f2+f3+f4)-(f6+f7+f8)}{(f1+f2+f8)-(f4+f5+f6)}\right\} \quad \text{[Expression 2]}$$

FIG. 5(b) illustrates a gradient vector in a case where an increment in an x-direction is 1 and an increment in a y-direction is −1. Thus, θ=tan$^{-1}$(−1)=315 degrees. Obviously, θ may also be described as −45 degrees depending on how θ is oriented.

Figure 6:
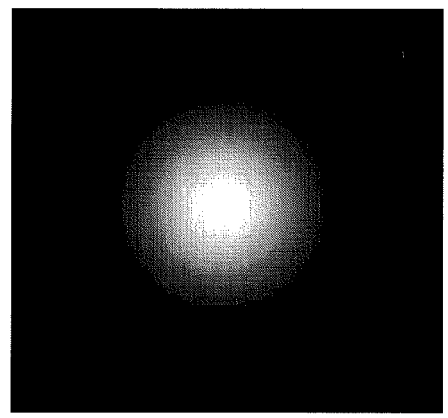
FIG. 6(a) illustrates an example of an input image according to the first embodiment.
FIG. 6(b) illustrates an example of an output image according to the first embodiment.
FIG. 6(c) illustrates another example of an output image according to the first embodiment.
Figure 6:
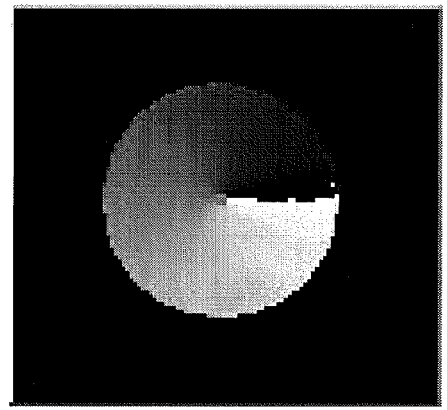
Figure 6:
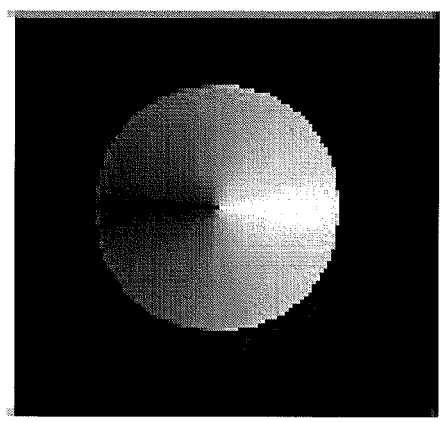

FIG. 6(a) illustrates a part of an input image. In this circular input image, luminance values are distributed such that the closer to a central portion, the higher the luminance value, and the closer to a peripheral portion, the lower the luminance value. According to this display method, since luminance value uniformly increases when approaching the central portion from any direction on a plane, a planar view is obtained.

FIG. 6(b) illustrates a situation in which angular information from 0 to 360 degrees is linearly transformed into luminance values ranging from 0 to 255 according to Expression 3 and displayed as an image.

$$\alpha = \theta \times \frac{255}{360} \quad (\theta = 0° \sim 360°) \quad \text{[Expression 3]}$$

As shown, by linearly transforming angular information obtained from a gradient vector into luminance values, a figure with a stereoscopic shape having angular dependency is obtained. However, since a domain of θ is set from 0 to 360 degrees for the image illustrated in FIG. 6(b), a fault plane of luminance variation has been formed.

In consideration thereof, in FIG. 6(c), angle-dependent information is assigned such that a location where a gradient vector indicates 0 degrees (360 degrees) is given a maximum luminance value of 255, luminance value becomes smaller the closer toward ±180 degrees from 0 degrees (360 degrees), and a central luminance value α is minimum at 180 degrees. In other words, a relationship between a size of the central luminance value α and θ can be expressed as in Expression 4.

$$\alpha = |\theta| \times \frac{255}{180} \quad (\theta = -180° \sim 180°) \quad \text{[Expression 4]}$$

In FIG. 6(c), a shadow has appeared that evokes a stereoscopic view created when light is illuminated from the direction of arrow A. Moreover, while FIG. 6(b) is not consistent with a real-life image, FIG. 6(b) has a similar significant effect to FIG. 6(c) in that characteristic points such as a point of luminance concentration having a gradient in the input image appear prominently.

In addition, another effect produced by assigning angle-dependent information is that contours are vividly displayed. Compared to an obscure contour in FIG. 6(a), contours are vividly displayed in FIGS. 6(b) and 6(c).

Next, an example of an adaptation of the above to a mammographic image will be shown.

Figure 7:
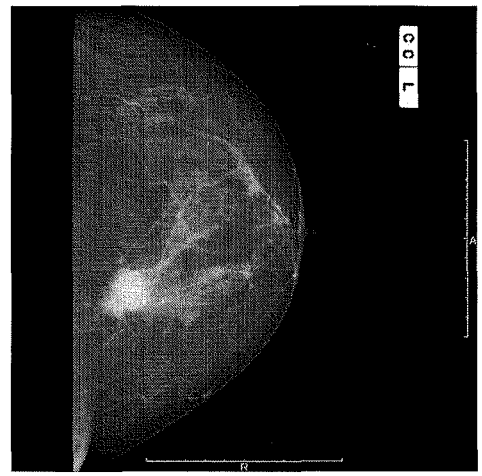
FIG. 7(a) illustrates an example of an input image that is an original image of mammography according to the second embodiment.
FIG. 7(b) illustrates an example of an output image according to the second embodiment.
FIG. 7(c) illustrates another example of an output image according to the second embodiment.
Figure 7:
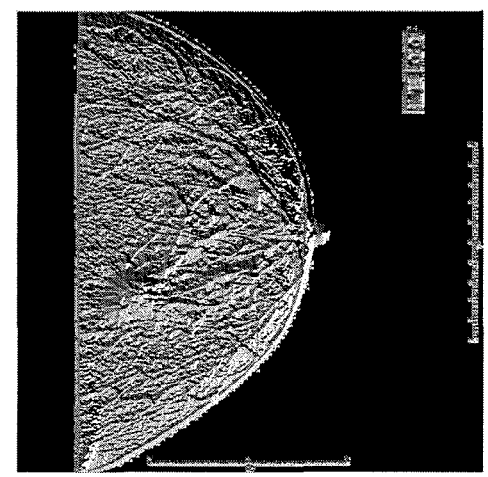
Figure 7:
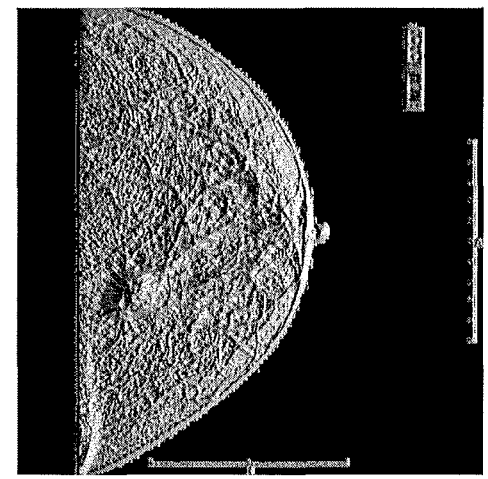

FIG. 7(a) illustrates an input image that is an original image of mammography.

FIGS. 7(b) and 7(c) illustrate output images obtained by respectively assigning angular dependency according to Expressions 3 and 4 to the image illustrated in FIG. 7(a). While domains of θ differ, FIGS. 7(b) and 7(c) share a common feature of being assigned angle-dependent information.

A point of luminance concentration in FIG. 7(a) is a mass accompanied by spiculae. In FIGS. 7(b) and 7(c), the point of luminance concentration is stereoscopically displayed and the characteristic point is displayed more vividly.

It is also worth noting that mammary glands and contours appear more vividly than in the original image.

In this manner, a portion having a luminance gradient in a planar input image is stereoscopically expressed and a characteristic portion of the input image is highlighted and displayed.

Third Embodiment

Edge Detection Processing Using a Laplacian Filter

In this embodiment, a method for performing edge detection by adapting a Laplacian filter to an output image of a conventionally-known iris filter will be described. An object of edge detection is to extract a characteristic portion of an image signal of each pixel included in an input image using a computer and perform so-called "marking" in which the characteristic portion is enclosed by a closed line.

Figure 8:
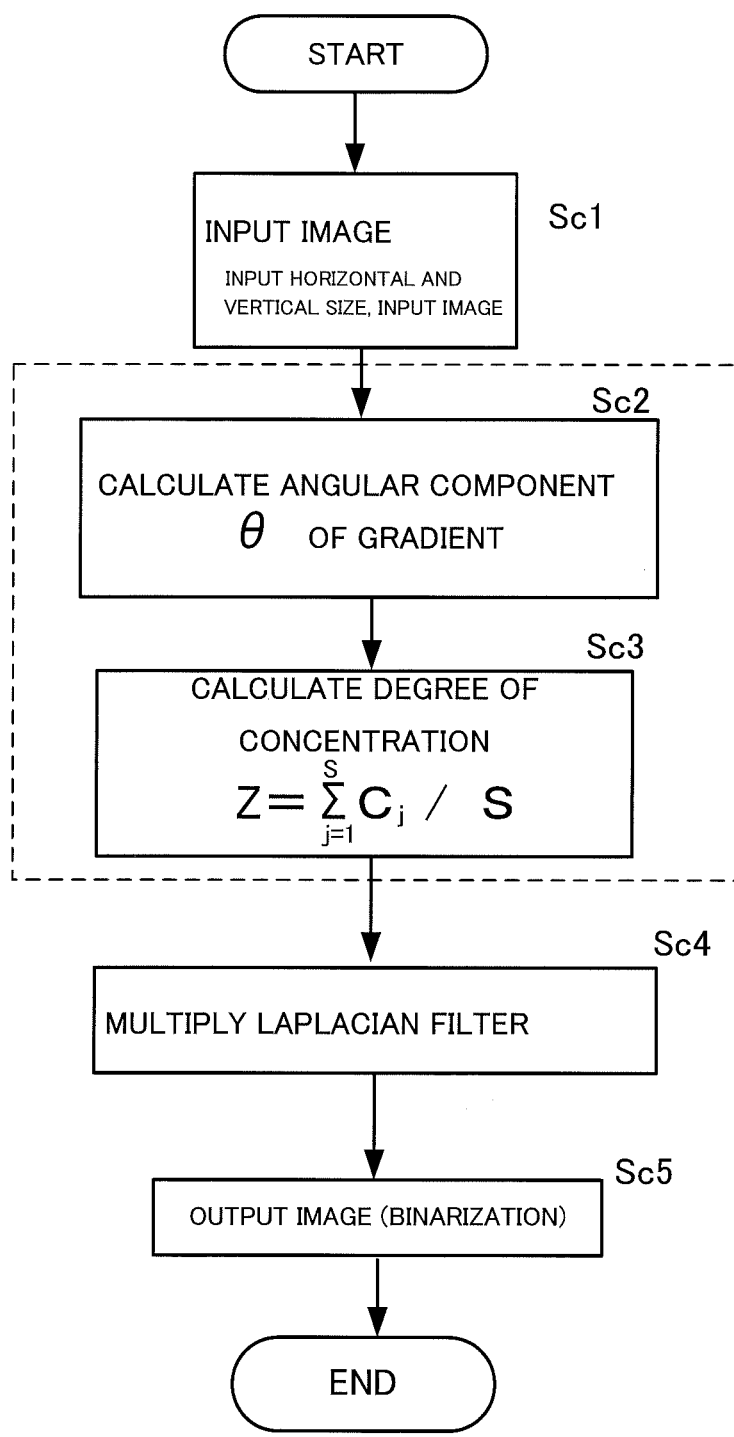
FIG. 8 is a diagram illustrating a procedure of an image processing method according to a third embodiment of the present invention.

FIG. 8 is a diagram illustrating a procedure of an image processing method according to a third embodiment of the present invention. Steps (Sc2) to (Sc3) represent a known algorithm referred to as an "iris filter" for obtaining a degree of concentration of an image signal such as a luminance value.

First, data of an input image is inputted into a computer, a closed region (x, y) made up of a plurality of pixels in the input image is demarcated as a target region C, a gradient vector is obtained from coordinates of a pixel of interest in the target region C and an arbitrarily defined neighboring pixel thereof by moving the target region C within the input image by predetermined pixel units, whereby a normalized value of an inner product obtained from the gradient vector of the two pixels, a unit vector oriented in a scanning direction of the target region C, and an angle θ formed by the gradient vector and the unit vector becomes a degree of concentration Z of the gradient vector.

A next step (Sc4) is an algorithm for multiplying a Laplacian filter.

Figure 9:
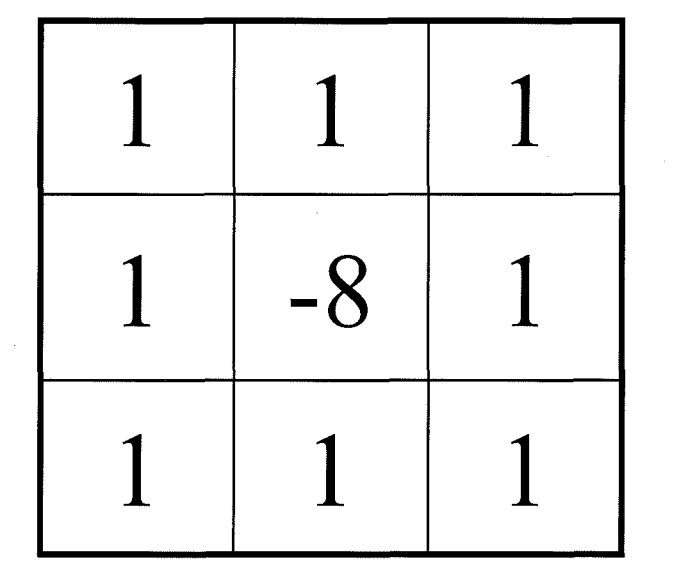

FIG. 9 illustrates an example of a Laplacian filter. As illustrated in the diagram, a so-called "8-neighbor Laplacian filter" which is a 3×3 mask having a central pixel whose value is −8 and neighboring pixels whose values are all 1 can be used as an operator of the Laplacian filter.

FIG. 9 illustrates an 8-neighbor Laplacian filter. As shown, processing is to be performed in eight directions, namely, the four directions of the pixels above, below, left, and right, as well as the four directions of diagonally-oriented pixels. After the Laplacian filter is multiplied, a binarization process is further performed to enhance edge portions.

Step (Sc5) is a step for performing a binarization process on the previous step (Sc4) to obtain an output image. All image signals of pixels whose degree of concentration calculation values are equal to or below a predetermined value are clipped to 0. Meanwhile, image signals of other pixels are either left as-is or linearly transformed to higher values.

Figure 10:
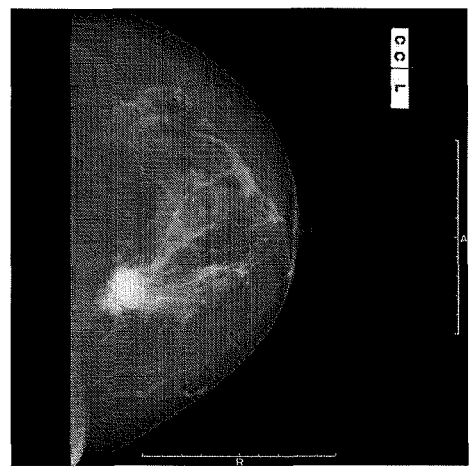
FIG. 10(a) illustrates an example of an input image that is an original image of mammography according to the third embodiment.
FIG. 10(b) illustrates an example of an output image according to the third embodiment.
FIG. 10(c) illustrates another example of an output image according to the third embodiment.
Figure 10:
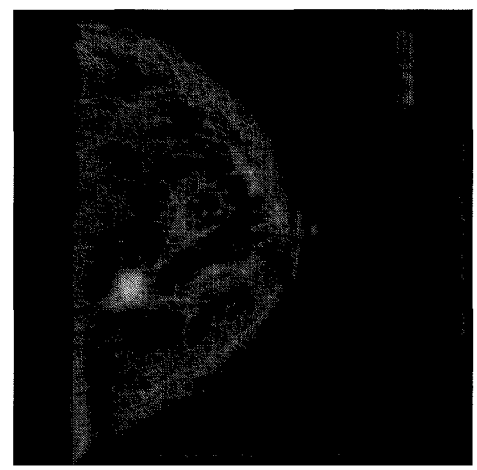
Figure 10:
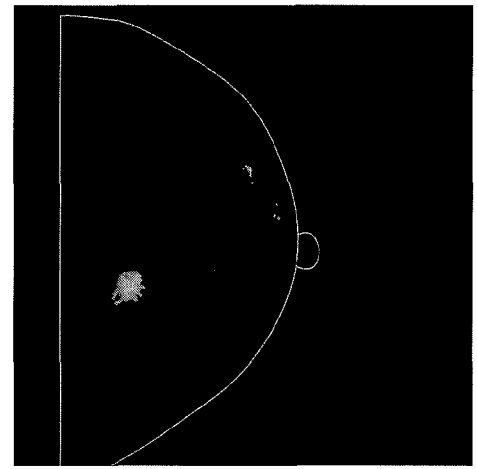

FIG. 10(a) illustrates an input image that is an original image of mammography. FIGS. 10(b) and 10(c) illustrate images in which only pixels with a predetermined luminance value have been extracted by applying threshold processing on an output image of iris filter processing (steps Sc2 to Sc3) performed according to the algorithm described above on the image illustrated on FIG. 10(a). FIG. 10(b) illustrates an output image for which pixels with degrees of concentration equal to or less than 0 have been clipped to 0 and, subsequently, luminance values of all other pixels have been multiplied by 320. In addition, FIG. 10(c) illustrates an output image displaying only regions with high degrees of concentration of FIG. 10(b) as an input image by clipping pixels whose luminance value is equal to or smaller than 100 to 0. Portions retained in FIG. 10(c) are mass shadows. However, while only a mass shadow actually remains, in order to clearly indicate a position of a mass, a contour of a breast is depicted by a dotted line in FIG. 10(c).

In order to mark the mass shadow, edge detection using a Laplacian filter is performed on the output image 2.

Figure 11:
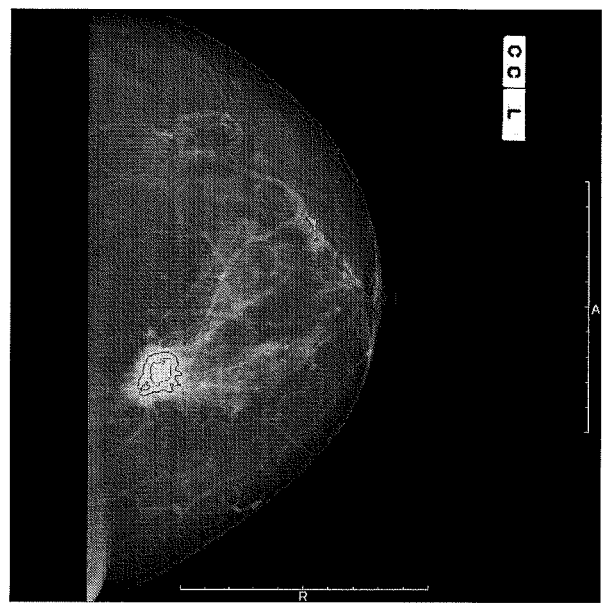
FIG. 11(a) illustrates an example of an output image subjected to edge detection using a Laplacian filter.
FIG. 11(b) is a schematic diagram of FIG. 11(a)
Figure 11:
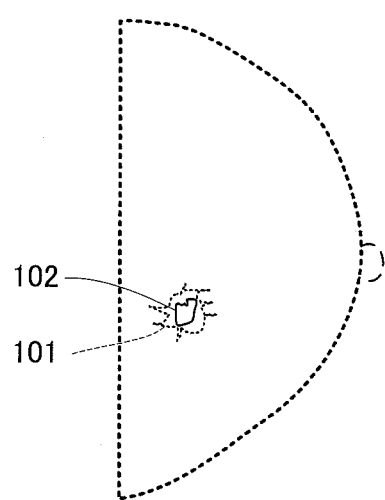

By performing the Laplacian operator on FIGS. 9(b) and 9(c) and then enhancing edge portions by performing a binarization process, an output image is obtained such as that illustrated in FIG. 11(a) in which marking is provided around the mass shadow of FIG. 11. In FIG. 11(b), outlines of marked portions and a breast are depicted by a solid line and a dashed line.

An outer mark 101 illustrated in FIG. 11(b) represents an output image obtained by performing a Laplacian filter operator process on the output image (FIG. 9(b)) resulting from applying an iris filter once on an input image, and an inner mark 102 illustrated in FIG. 11(b) represents an output image obtained by performing a Laplacian filter operator process on the output image (FIG. 9(c)) resulting from applying an iris filter twice on the input image.

The outer mark 101 is displayed for retrieving all mass shadow candidates without omission, while the inner mark 102 indicates mass shadows having a higher likelihood of being actual masses among the retrieved mass shadows.

Fourth Embodiment

A fourth embodiment represents a mode for providing a computer program for realizing the image processing method according to the present invention as an image processing application program to be executed on a computer such as a personal computer.

Figure 12:
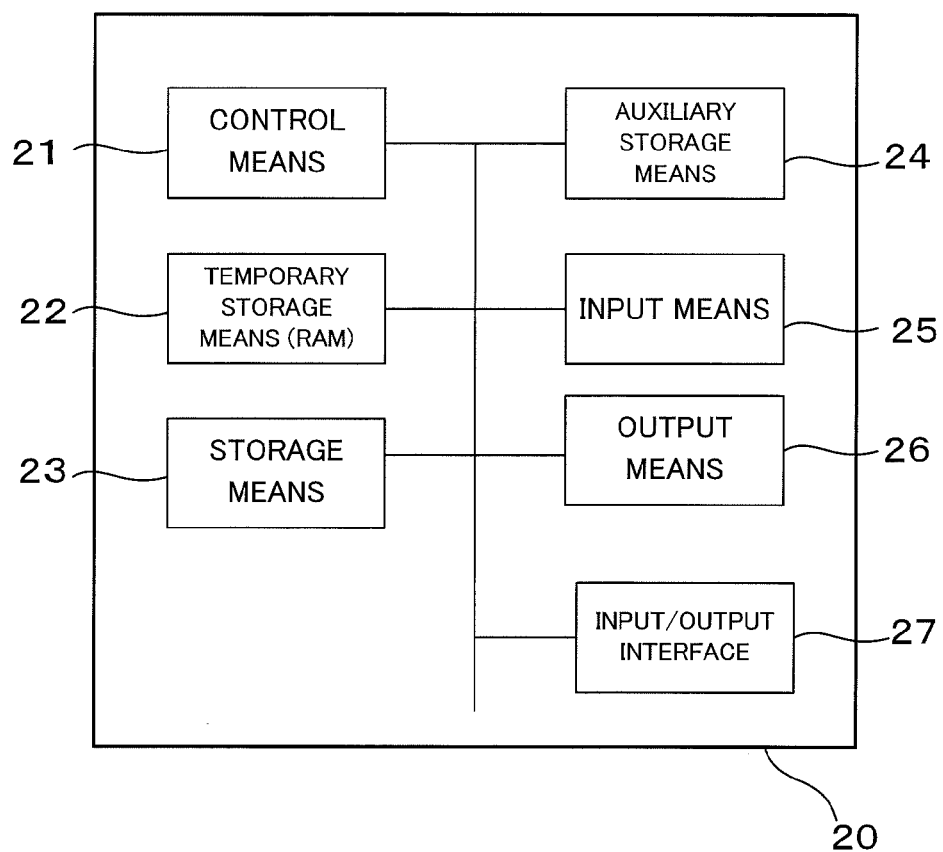
FIG. 12 is a block diagram illustrating a configuration of an image processing apparatus according to a fourth embodiment of the present invention.

FIG. 12 is a block diagram illustrating a configuration of an image processing apparatus according to the fourth embodiment of the present invention. An image processing apparatus 20 in which is installed a program for causing a personal computer to execute the respective steps of the respective image processing methods according to the present invention includes a CPU (Central Processing Unit) 21 for controlling the entire apparatus, temporary storage means 22 such as a RAM (Random Access Memory), storage means 23 such as a hard disk, auxiliary storage means 24 such as an optical disk drive for reading various data from a storage medium, input means 25 such as a mouse and a keyboard, and output means 26 such as a monitor or a printer. By loading the computer program according to the present invention recorded on a storage medium onto the storage means 23 and executing the computer program on an operating system under the control of the control means 21, the personal computer operates as the image processing apparatus 20 according to the present invention.

In the image processing apparatus 20, by executing the computer program stored in the storage means 22 under the control of the control means 21 and executing the respective steps described in the first to third embodiments, image processing is performed on an image stored in the storage means 23 or the like or an image inputted via an interface 27 to the outside and an output image is outputted from the output means 26.

Expectations are high for the application of the image processing method according to the present invention to support systems for medical diagnosis such as mammography and to usage such as displaying inconspicuous portions or characteristic portions more clearly. Therefore, the industrial applicability of the present invention is extremely high.

What is claimed is:

1. An image processing method for adjusting a size of an image signal of each pixel included in an input image by a computer according to a predetermined purpose, the image processing method comprising the steps of:

(Sa1) inputting data of an input image into a computer;
 (Sa2) inputting an arbitrarily defined constant m as a contrast intensity;
 (Sa3) demarcating a closed region made up of a plurality of pixels in the input image as a target region D, summing degrees of inclination between respective two pixels, namely, a pixel of interest in the target region D and arbitrarily defined neighboring pixels thereof, over a whole circumference around the pixel of interest, and dividing the sum by the number of pixels within the target region to calculate a mean value thereof, wherein the mean value is an amplitude β of a gradient; and
 (Sa4) multiplying the amplitude value β of a gradient obtained in step (Sa3) by the contrast intensity m (where m is a positive constant) inputted in step (Sa2) and adding an arbitrarily defined offset value γ to the obtained value, wherein $$\beta = \frac{1}{N} \sum_{i=-k}^{k} \sum_{j=-k}^{k} (x_{(i=0, j=0)} - x_{(i,j)})$$

i is an index corresponding to a first spatial dimension,
j is an index corresponding to a second spatial dimension,
k is an arbitrarily defined boundary constant greater than or equal to one,
$x_{(i,j)}$ corresponds to the pixels of the target region D,
target region D is bounded in one corner by a pixel corresponding to $x_{(i=-k, j=-k)}$ and in another corner by a pixel corresponding to $x_{(i=k, j=k)}$,
N is the number of pixels in the target region D,
$x_{(i=0, j=0)}$ corresponds to the pixel of interest in the target region D, and
$x_{(i\neq 0, j\neq 0)}$ corresponds to the arbitrarily defined neighboring pixels of target region D;
the method further including repeating (Sa3) and (Sa4) with respect to a new target region D and new pixel of interest in the new target region D.

2. An article comprising a non-transitory computer-readable medium that stores computer-executable instructions that, when read by a computer, cause the computer to execute the respective steps according to claim 1.

* * * * *